(12) United States Patent
Kane et al.

(10) Patent No.: US 12,329,977 B2
(45) Date of Patent: *Jun. 17, 2025

(54) CATHETER AND LEADLESS CARDIAC DEVICES INCLUDING ELECTRICAL PATHWAY BARRIER

(71) Applicant: CARDIAC PACEMAKERS, INC., St. Paul, MN (US)

(72) Inventors: Michael J. Kane, St. Paul, MN (US); Brian L. Schmidt, White Bear Lake, MN (US); Kevin G. Wika, Blaine, MN (US)

(73) Assignee: CARDIAC PACEMAKERS, INC.

( * ) Notice: Subject to any disclaimer, the term of this patent is extended or adjusted under 35 U.S.C. 154(b) by 680 days.

This patent is subject to a terminal disclaimer.

(21) Appl. No.: 17/521,051

(22) Filed: Nov. 8, 2021

(65) Prior Publication Data

US 2022/0054847 A1 Feb. 24, 2022

Related U.S. Application Data

(63) Continuation of application No. 15/817,678, filed on Nov. 20, 2017, now Pat. No. 11,198,013.

(Continued)

(51) Int. Cl.
*A61N 1/375* (2006.01)
*A61M 25/00* (2006.01)
*A61N 1/372* (2006.01)

(52) U.S. Cl.
CPC ..... *A61N 1/37512* (2017.08); *A61M 25/0097* (2013.01); *A61N 1/372* (2013.01); *A61N 1/3756* (2013.01)

(58) Field of Classification Search
CPC .. A61N 1/3752; A61N 1/3754; A61N 1/3756; A61N 1/3758; A61N 1/37512; A61N 1/372; A61M 25/0097
See application file for complete search history.

(56) References Cited

U.S. PATENT DOCUMENTS 4,301,815 A 11/1981 Doring
5,807,399 A 9/1998 Laske et al.
(Continued)

FOREIGN PATENT DOCUMENTS

EP 2818201 B1 7/2016
EP 2658599 B1 10/2016
(Continued)

*Primary Examiner* — Shirley X Jian
(74) *Attorney, Agent, or Firm* — Seager, Tufte & Wickhem LLP

(57) ABSTRACT

Catheter and implantable leadless pacing devices, systems, and methods utilizing catheters and implantable leadless pacing devices are disclosed. An example catheter system may include a holding structure extending distally from a tubular member. An implantable device, such a leadless pacing device, may be located within a cavity of the holding structure and an electrical barrier may be located within the holding structure at a location between a proximal electrode and a distal electrode of the implantable device. The electrical barrier may inhibit electrical signals of the implantable device from traveling within the holding structure between the proximal electrode and the distal electrode of the implantable device. The holding structure may include one or more electrical ports adjacent the proximal end of the holding structure and adjacent or proximal of the proximal electrode of the implantable device.

17 Claims, 15 Drawing Sheets

Related U.S. Application Data

(60) Provisional application No. 62/424,760, filed on Nov. 21, 2016.

(56) References Cited

U.S. PATENT DOCUMENTS

| | | | |
|---|---|---|---|
| 5,908,381 A | 6/1999 | Aznoian et al. | |
| 5,916,158 A * | 6/1999 | Webster, Jr. | A61N 1/056 606/41 |
| 6,181,973 B1 | 1/2001 | Ceron et al. | |
| 6,395,017 B1 | 5/2002 | Dwyer et al. | |
| 6,409,674 B1 | 6/2002 | Brockway et al. | |
| 6,582,441 B1 | 6/2003 | He et al. | |
| 6,638,268 B2 | 10/2003 | Niazi | |
| 6,786,918 B1 | 9/2004 | Krivoruchko et al. | |
| 7,381,216 B2 | 6/2008 | Buzzard et al. | |
| 7,499,758 B2 | 3/2009 | Cates et al. | |
| 7,509,169 B2 | 3/2009 | Eigler et al. | |
| 7,608,099 B2 | 10/2009 | Johnson et al. | |
| 7,799,037 B1 | 9/2010 | He et al. | |
| 7,840,281 B2 | 11/2010 | Kveen et al. | |
| 7,993,351 B2 | 8/2011 | Worley et al. | |
| 8,010,209 B2 | 8/2011 | Jacobson | |
| 8,103,361 B2 | 1/2012 | Moser | |
| 8,185,213 B2 | 5/2012 | Kveen et al. | |
| 8,267,987 B2 | 9/2012 | Johnson et al. | |
| 8,352,028 B2 | 1/2013 | Wenger | |
| 8,364,280 B2 | 1/2013 | Marnfeldt et al. | |
| 8,382,813 B2 | 2/2013 | Shumer et al. | |
| 8,428,750 B2 | 4/2013 | Kolberg | |
| 8,478,431 B2 | 7/2013 | Griswold et al. | |
| 8,504,156 B2 | 8/2013 | Bonner et al. | |
| 8,527,068 B2 | 9/2013 | Ostroff | |
| 8,532,790 B2 | 9/2013 | Griswold | |
| 8,548,605 B2 | 10/2013 | Ollivier | |
| 8,615,310 B2 | 12/2013 | Khairkhahan et al. | |
| 8,634,912 B2 | 1/2014 | Bornzin et al. | |
| 8,721,587 B2 | 5/2014 | Berthiaume et al. | |
| 8,727,996 B2 | 5/2014 | Allan et al. | |
| 8,758,365 B2 | 6/2014 | Bonner et al. | |
| 8,855,789 B2 | 10/2014 | Jacobson | |
| 8,903,513 B2 | 12/2014 | Ollivier | |
| 8,926,588 B2 | 1/2015 | Berthiaume et al. | |
| 8,945,145 B2 | 2/2015 | Tran et al. | |
| 8,945,146 B2 | 2/2015 | Steingisser et al. | |
| 8,948,883 B2 | 2/2015 | Eggen et al. | |
| 8,958,892 B2 | 2/2015 | Khairkhahan et al. | |
| 9,020,611 B2 | 4/2015 | Khairkhahan et al. | |
| 9,072,872 B2 | 7/2015 | Asleson et al. | |
| 9,101,281 B2 | 8/2015 | Reinert et al. | |
| 9,119,959 B2 | 9/2015 | Rys et al. | |
| 9,126,032 B2 | 9/2015 | Khairkhahan et al. | |
| 9,155,882 B2 | 10/2015 | Grubac et al. | |
| 9,168,372 B2 | 10/2015 | Fain | |
| 9,204,842 B2 | 12/2015 | Mothilal et al. | |
| 9,205,225 B2 | 12/2015 | Khairkhahan et al. | |
| 9,216,293 B2 | 12/2015 | Berthiaume et al. | |
| 9,220,906 B2 | 12/2015 | Griswold et al. | |
| 9,238,145 B2 | 1/2016 | Wenzel et al. | |
| 9,242,102 B2 | 1/2016 | Khairkhahan et al. | |
| 9,272,155 B2 | 3/2016 | Ostroff | |
| 9,283,381 B2 | 3/2016 | Grubac et al. | |
| 9,283,382 B2 | 3/2016 | Berthiaume et al. | |
| 9,283,392 B2 | 3/2016 | Moore et al. | |
| 9,308,365 B2 | 4/2016 | Nordstrom et al. | |
| 9,308,374 B2 | 4/2016 | Kveen et al. | |
| 9,339,197 B2 | 5/2016 | Griswold et al. | |
| 9,351,648 B2 | 5/2016 | Mothilal et al. | |
| 9,358,387 B2 | 6/2016 | Suwito et al. | |
| 9,414,857 B2 | 8/2016 | Wood et al. | |
| 9,421,384 B2 | 8/2016 | Taff et al. | |
| 9,433,780 B2 | 9/2016 | Régnier et al. | |
| 9,446,248 B2 | 9/2016 | Sheldon et al. | |
| 9,463,315 B2 | 10/2016 | Bornzin et al. | |
| 9,468,773 B1 | 10/2016 | Anderson et al. | |
| 9,504,820 B2 | 11/2016 | Bonner et al. | |
| 9,511,236 B2 | 12/2016 | Varady et al. | |
| 9,517,336 B2 | 12/2016 | Eggen et al. | |
| 9,517,337 B2 | 12/2016 | Ollivier | |
| 9,526,522 B2 | 12/2016 | Wood et al. | |
| 9,526,891 B2 | 12/2016 | Eggen et al. | |
| 9,539,423 B2 | 1/2017 | Bonner et al. | |
| 9,555,236 B2 | 1/2017 | Régnier et al. | |
| 9,579,500 B2 | 2/2017 | Rys et al. | |
| 9,610,454 B2 | 4/2017 | Doan et al. | |
| 9,623,234 B2 | 4/2017 | Anderson | |
| 9,662,487 B2 | 5/2017 | Kveen et al. | |
| 9,675,798 B2 | 6/2017 | Grubac et al. | |
| 9,717,421 B2 | 8/2017 | Griswold et al. | |
| 9,724,507 B2 | 8/2017 | Wood et al. | |
| 9,750,931 B2 | 9/2017 | Wood et al. | |
| 9,764,139 B2 | 9/2017 | Christensen | |
| 9,775,982 B2 | 10/2017 | Grubac et al. | |
| 9,808,617 B2 | 11/2017 | Ostroff et al. | |
| 9,808,629 B2 | 11/2017 | Steingisser et al. | |
| 9,814,896 B2 | 11/2017 | Solem | |
| 9,833,625 B2 | 12/2017 | Waldhauser et al. | |
| 9,833,626 B2 | 12/2017 | Klimovitch et al. | |
| 9,844,659 B2 | 12/2017 | Grubac et al. | |
| 9,844,664 B2 | 12/2017 | McEvoy et al. | |
| 9,861,815 B2 | 1/2018 | Tran et al. | |
| 9,867,982 B2 | 1/2018 | Berthiaume et al. | |
| 10,722,684 B2 * | 7/2020 | Soltis | A61N 1/0587 |
| 10,981,008 B2 * | 4/2021 | Schmidt | A61N 1/3756 |
| 11,198,013 B2 * | 12/2021 | Kane | A61N 1/37512 |
| 2005/0209653 A1 | 9/2005 | Herbert et al. | |
| 2005/0267555 A1 | 12/2005 | Marnfeldt et al. | |
| 2009/0082828 A1 | 3/2009 | Ostroff | |
| 2010/0274227 A1 | 10/2010 | Khairkhahan et al. | |
| 2011/0112548 A1 | 5/2011 | Fifer et al. | |
| 2011/0270339 A1 | 11/2011 | Murray, III et al. | |
| 2011/0270340 A1 | 11/2011 | Pellegrini et al. | |
| 2012/0095539 A1 | 4/2012 | Khairkhahan et al. | |
| 2012/0109148 A1 | 5/2012 | Bonner et al. | |
| 2012/0172690 A1 | 7/2012 | Anderson et al. | |
| 2012/0172891 A1 | 7/2012 | Lee | |
| 2013/0035636 A1 | 2/2013 | Beasley et al. | |
| 2013/0103047 A1 | 4/2013 | Steingisser et al. | |
| 2013/0131591 A1 | 5/2013 | Berthiaume et al. | |
| 2013/0253342 A1 | 9/2013 | Griswold et al. | |
| 2013/0253346 A1 | 9/2013 | Griswold et al. | |
| 2014/0018818 A1 | 1/2014 | Somogyi et al. | |
| 2014/0324145 A1 | 10/2014 | Eggen et al. | |
| 2014/0378991 A1 | 12/2014 | Ollivier | |
| 2015/0039070 A1 | 2/2015 | Kuhn et al. | |
| 2015/0045868 A1 | 2/2015 | Bonner et al. | |
| 2015/0051615 A1 * | 2/2015 | Schmidt | A61N 1/3756 606/129 |
| 2015/0094735 A1 | 4/2015 | Ward et al. | |
| 2015/0283376 A1 | 10/2015 | Ollivier et al. | |
| 2015/0306381 A1 | 10/2015 | Schmidt et al. | |
| 2015/0335884 A1 | 11/2015 | Khairkhahan et al. | |
| 2015/0352351 A1 | 12/2015 | Muessig et al. | |
| 2016/0000563 A1 | 1/2016 | Asleson et al. | |
| 2016/0015287 A1 | 1/2016 | Anderson et al. | |
| 2016/0015322 A1 | 1/2016 | Anderson et al. | |
| 2016/0059003 A1 | 3/2016 | Eggen et al. | |
| 2016/0067446 A1 | 3/2016 | Klenk et al. | |
| 2016/0067447 A1 | 3/2016 | Paspa et al. | |
| 2016/0067503 A1 | 3/2016 | Berthiaume et al. | |
| 2016/0082270 A1 | 3/2016 | Mothilal et al. | |
| 2016/0096001 A1 | 4/2016 | Eidenschink et al. | |
| 2016/0158560 A1 | 6/2016 | Moore et al. | |
| 2016/0206872 A1 | 7/2016 | Wood et al. | |
| 2016/0213919 A1 | 7/2016 | Suwito et al. | |
| 2016/0220829 A1 | 8/2016 | Wood | |
| 2016/0228715 A9 | 8/2016 | Bonner et al. | |
| 2016/0235971 A1 | 8/2016 | Wood et al. | |
| 2016/0243350 A9 | 8/2016 | Grubac et al. | |
| 2016/0243355 A1 | 8/2016 | Wood | |
| 2016/0263372 A1 | 9/2016 | Wood et al. | |
| 2016/0271388 A1 | 9/2016 | Ollivier et al. | |
| 2016/0279423 A1 | 9/2016 | Kelly et al. | |
| 2016/0296761 A1 | 10/2016 | Doan et al. | |

(56) References Cited

U.S. PATENT DOCUMENTS

| | | |
|---|---|---|
| 2016/0310703 A1 | 10/2016 | Drake et al. |
| 2016/0310723 A1 | 10/2016 | Eggen et al. |
| 2016/0310726 A1 | 10/2016 | Demmer et al. |
| 2016/0310747 A1 | 10/2016 | Grubac et al. |
| 2016/0325104 A1 | 11/2016 | Anderson et al. |
| 2016/0361536 A1 | 12/2016 | Grubac et al. |
| 2017/0028190 A1 | 2/2017 | O'Carroll et al. |
| 2017/0028194 A1 | 2/2017 | Bonner et al. |
| 2017/0043158 A1 | 2/2017 | Kelly et al. |
| 2017/0065369 A1 | 3/2017 | Bornzin et al. |
| 2017/0072191 A1 | 3/2017 | Ma et al. |
| 2017/0095662 A1 | 4/2017 | McDonnell et al. |
| 2017/0100582 A1 | 4/2017 | McEvoy et al. |
| 2017/0106185 A1 | 4/2017 | Orts et al. |
| 2017/0113035 A1 | 4/2017 | Bonner et al. |
| 2017/0119999 A1 | 5/2017 | Kelly |
| 2017/0136231 A1 | 5/2017 | Kelly et al. |
| 2017/0143980 A1 | 5/2017 | Soltis et al. |
| 2017/0151429 A1 | 6/2017 | Regnier |
| 2017/0165479 A1 | 6/2017 | Rys et al. |
| 2017/0189681 A1 | 7/2017 | Anderson |
| 2017/0209688 A1 | 7/2017 | Drake et al. |
| 2017/0209689 A1 | 7/2017 | Chen et al. |
| 2017/0209690 A1 | 7/2017 | Drake et al. |
| 2017/0216575 A1 | 8/2017 | Asleson et al. |
| 2017/0224997 A1 | 8/2017 | Shuros et al. |
| 2017/0274202 A1 | 9/2017 | Grubac et al. |
| 2017/0304624 A1 | 10/2017 | Friedman et al. |
| 2017/0312479 A1 | 11/2017 | Keaveney et al. |
| 2017/0312496 A1 | 11/2017 | Wood et al. |
| 2017/0319847 A1 | 11/2017 | Ho et al. |
| 2017/0326369 A1 | 11/2017 | Koop et al. |
| 2017/0326372 A1 | 11/2017 | Koop et al. |
| 2017/0326373 A1 | 11/2017 | Delanely, Jr. et al. |
| 2017/0340316 A1 | 11/2017 | Wood et al. |
| 2017/0340877 A1 | 11/2017 | Ollivier |
| 2017/0368338 A1 | 12/2017 | Madden et al. |
| 2018/0177979 A1* | 6/2018 | Soltis ................. A61N 1/37211 |
| 2022/0387806 A1* | 12/2022 | McCormick ......... A61N 1/3787 |

FOREIGN PATENT DOCUMENTS

| | | |
|---|---|---|
| EP | 2651502 B1 | 11/2016 |
| EP | 2771064 B1 | 1/2017 |
| EP | 2780077 B1 | 1/2017 |
| WO | 2012082755 A1 | 6/2012 |

* cited by examiner

CATHETER AND LEADLESS CARDIAC DEVICES INCLUDING ELECTRICAL PATHWAY BARRIER

CROSS REFERENCE TO RELATED APPLICATIONS

This application is a continuation of U.S. application Ser. No. 15/817,678, filed on Nov. 20, 2017, issued as U.S. Pat. No. 11,198,013, which claims the benefit of and priority to U.S. Provisional Patent Application Ser. No. 62/424,760, filed on Nov. 21, 2016, the disclosures of which are incorporated herein by reference.

TECHNICAL FIELD

The present disclosure pertains to medical devices, and methods for manufacturing and/or using medical devices. More particularly, the present disclosure pertains to leadless cardiac devices and methods, such as leadless pacing devices and methods, and delivery devices and methods for such leadless devices.

BACKGROUND

A wide variety of medical devices have been developed for medical use, for example, cardiac use. Some of these devices include catheters, leads, pacemakers, and the like, and delivery devices and/or systems used for delivering such devices. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

BRIEF SUMMARY

This disclosure provides design, material, manufacturing method, and use alternatives for medical devices, including catheters and implantable devices.

In a first example, a catheter system for carrying an implantable leadless pacing device may comprise a tubular member including a lumen extending from a proximal end to a distal end thereof, a tubular distal holding structure extending distally of the distal end of the tubular member and defining a cavity, a leadless pacing device located at least partially within the cavity and having a proximal electrode and a distal electrode, and an electrical barrier at an axial location between the proximal electrode and the distal electrode of the leadless pacing device. The electrical barrier inhibits electrical signals of the leadless pacing device from traveling within the tubular distal holding structure between the proximal electrode of the leadless pacing device and the distal electrode of the leadless pacing device.

Alternatively or additionally to any of the examples above, in another example, the catheter system may comprise an electrical port extending through the tubular distal holding structure at a location proximal of the proximal electrode of the leadless pacing device.

Alternatively or additionally to any of the examples above, in another example, the catheter system may comprise a hub secured to the tubular member and a body portion secured to the hub and extending distally from the hub, wherein the body portion at least partially defines the cavity.

Alternatively or additionally to any of the examples above, in another example, the catheter system may comprise an electrical port extending through the body portion.

Alternatively or additionally to any of the examples above, in another example, the catheter system may comprise an electrical port extending through the hub.

Alternatively or additionally to any of the examples above, in another example, the electrical barrier is affixed to and extends from the tubular distal holding structure.

Alternatively or additionally to any of the examples above, in another example, the electrical barrier is affixed to and extends from the leadless pacing device.

Alternatively or additionally to any of the examples above, in another example, the electrical barrier is a ring filling a radial space between an outer surface of the leadless pacing device and an inner surface of the tubular distal holding structure.

Alternatively or additionally to any of the examples above, in another example, the electrical barrier comprises a non-conductive gel filler at least partially filling a radial space between an exterior surface of the leadless pacing device and an inner surface of the tubular distal holding structure.

Alternatively or additionally to any of the examples above, in another example, the electrical barrier has a first portion having a first tension or stiffness and a second portion having a second tension or stiffness different than the first tension or stiffness.

Alternatively or additionally to any of the examples above, in another example, the first tension or stiffness is less than the second tension or stiffness and the first portion flexes or deflects to allow a fluid to pass through the electrical barrier in response to applying a pressure greater than a threshold pressure to the first portion.

Alternatively or additionally to any of the examples above, in another example, the distal holding structure comprises a reduced diameter portion of the tubular distal holding structure circumferentially contacting the leadless pacing device to form the electrical barrier.

Alternatively or additionally to any of the examples above, in another example, the tubular distal holding structure comprises a braid having a tightened portion shaping the reduced diameter portion.

Alternatively or additionally to any of the examples above, in another example, the braid is made from nitinol and the reduced diameter portion is configured to change shape in response to a pressure greater than a threshold pressure being applied to a proximal side of the reduced diameter portion.

In another example, a catheter for carrying an implantable leadless pacing device may comprise a tubular member including a lumen extending from a proximal end to a distal end thereof, a tubular distal holding structure extending distally of the distal end of the tubular member and defining a cavity, an electrical port extending through a proximal portion of the tubular distal holding structure, and an electrical barrier at an axial location between the proximal portion and a distal portion of the tubular distal holding structure. The electrical barrier inhibits electrical signals from crossing the axial location of the electrical barrier when a leadless pacing device is received within the tubular distal holding structure.

Alternatively or additionally to any of the examples above, in another example, the electrical barrier is actuatable to allow a fluid to cross an axial location of the electrical barrier when a leadless pacing device is received within the tubular distal holding structure.

Alternatively or additionally to any of the examples above, in another example, the electrical barrier comprises a ring extending from an inner surface of the tubular distal holding structure.

Alternatively or additionally to any of the examples above, in another example, the catheter may comprise a hub attached to and extending distally from the tubular member and a body portion attached to and extending distally from the hub, wherein the electrical port extends through one or more of the hub and the body portion to allow electrical signals to pass from interior the tubular distal holding structure to exterior the tubular distal holding structure.

In another example, a method of directing electrical signals from a leadless pacing device received in a tubular distal holding structure attached to a distal end of a tubular member comprises emitting electrical signals from a first electrode of a leadless pacing device received in a tubular distal holding structure of a delivery catheter, directing the emitted electrical signals exterior of the distal holding structure through electrical ports in the tubular distal holding structure at a location proximal of the first electrode of the leadless pacing device, and receiving the emitted electrical signal directed exterior of the distal holding structure at a second electrode of the leadless pacing device within the distal holding structure, wherein the second electrode of the leadless pacing device is located distal of the first electrode of the leadless pacing device.

Alternatively or additionally to any of the examples above, in another example, the method may comprise directing the emitted electrical signals through the electrical ports using an electrical barrier to inhibit signals from traveling within the tubular distal holding structure between the first electrode of the leadless pacing device and the second electrode of the leadless pacing device.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

The disclosure may be more completely understood in consideration of the following detailed description in connection with the accompanying drawings, in which.

Figure 1:
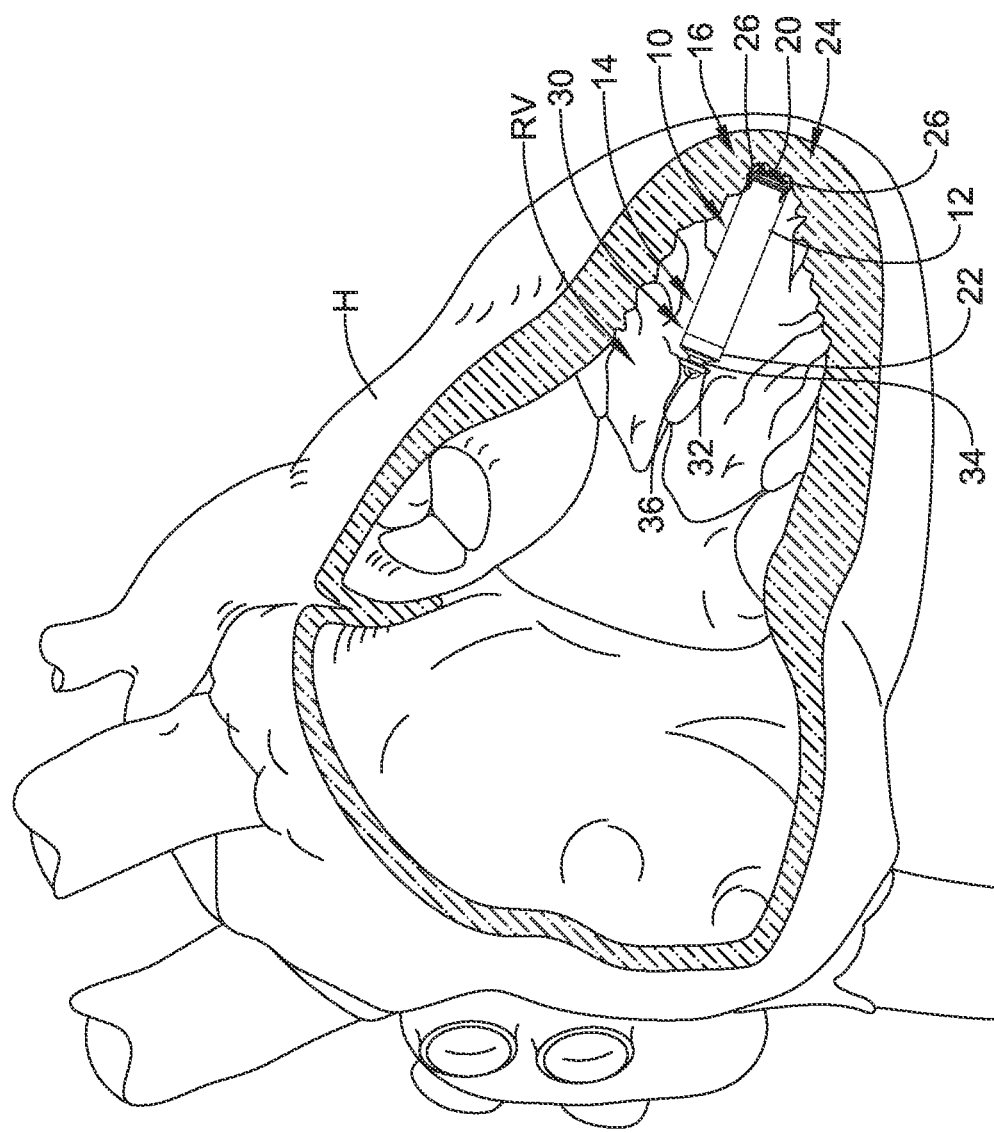
FIG. 1 is a plan view of an example leadless pacing device implanted within a heart.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition. The capsule may be delivered to the heart using a delivery device which may be advanced through a femoral vein, into the inferior vena cava, into the right atrium, through the tricuspid valve, and into the right ventricle. Accordingly, it may be desirable to provide delivery devices which facilitate advancement through the vasculature.

Figure 2:
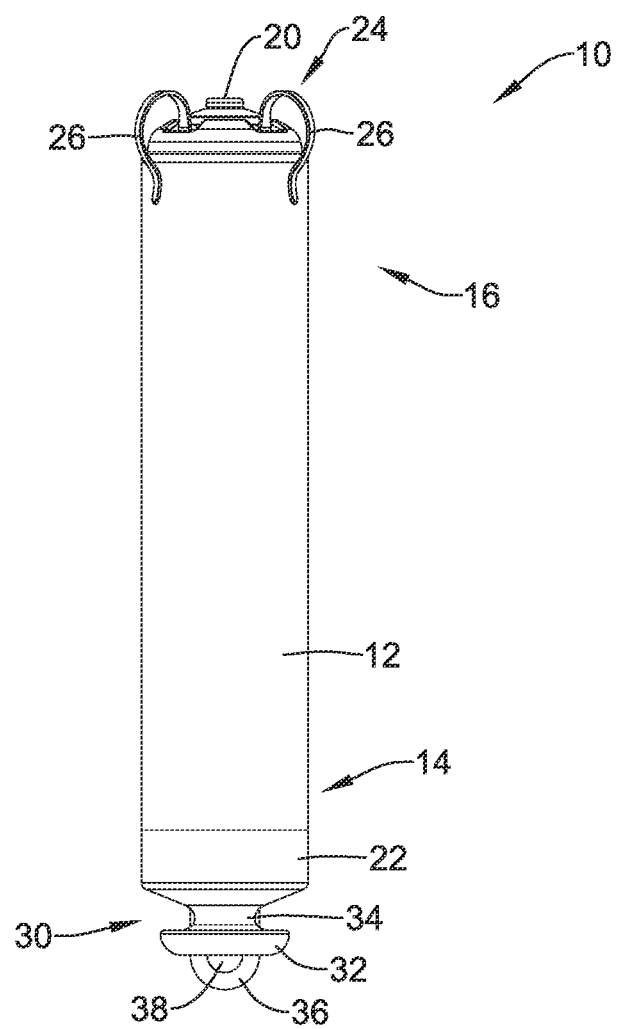
FIG. 2 is a side view of an example implantable leadless cardiac pacing device.

FIG. 1 illustrates an example implantable leadless cardiac pacing device 10 (e.g., a leadless pacemaker) implanted in a chamber of a heart H, such as the right ventricle RV. A side view of the illustrative implantable device 10 is shown in FIG. 2. The implantable device 10 may include a shell or housing 12 having a proximal end 14 and a distal end 16. The implantable device 10 may include a first electrode 20 positioned adjacent to the distal end 16 of the housing 12 and a second electrode 22 positioned adjacent to the proximal end 14 of the housing 12. For example, housing 12 may include a conductive material and may be insulated along a portion of its length. A section along the proximal end 14 may be free of insulation so as to define the second electrode 22. The electrodes 20, 22 may be sensing and/or pacing electrodes to provide electro-therapy and/or sensing capabilities. The first electrode 20 may be capable of being positioned against or may otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between the pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more hooks or tines 26 anchored into the cardiac tissue of the heart H to attach the implantable device 10 to a tissue wall. In other instances, the fixation mechanism 24 may include one or more passive tines configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. Although the docking member 30 may take on various forms, the docking member 30 may, for example, extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion 34 from the longitudinal axis of the implantable device 10.

The docking member 30 may further include a tether retention structure 36 extending from the head portion 32. The tether retention structure 36 may define an opening 38 configured to receive a tether or other anchoring mechanism therethrough. While the retention structure 36 is shown as having a generally "U-shaped" configuration, the retention structure 36 may take any shape which provides an enclosed perimeter surrounding the opening 38 such that a tether may be securably and releasably passed (e.g. looped) through the opening 38. The retention structure 36 may extend though the head portion 32, along the neck portion 34, and to or into the proximal end 14 of the housing 12, but this is not required.

The docking member 30 may be configured to facilitate delivery of the implantable device 10 to the intracardiac site and/or retrieval of the implantable device 10 from the intracardiac site. Docking members 30, other than those described above, are contemplated.

One aspect of the current disclosure relates to the delivery device and/or system used, for example, to deliver device 10 to a suitable location within the anatomy (e.g., the heart). As may be appreciated, the delivery device may need to be navigated through relatively tortuous anatomy to deliver the device 10 to a suitable location. For instance, in some embodiments, the delivery device may be advanced through the vasculature to a target region. In some example cases the device may be advanced through a femoral vein, into the inferior vena cava, into the right atrium, through the tricuspid valve, and into the right ventricle. The target region for the delivery of the device 10 may be a portion of the right ventricle, for example, a portion of the right ventricle near the apex of the heart. The target region may also include other regions of the heart (e.g., right atrium, left atrium, or left ventricle), blood vessels, or other suitable targets. It may be desirable to provide the delivery system with certain features that may allow for easier or better control for navigation or delivery purposes.

Figure 3:
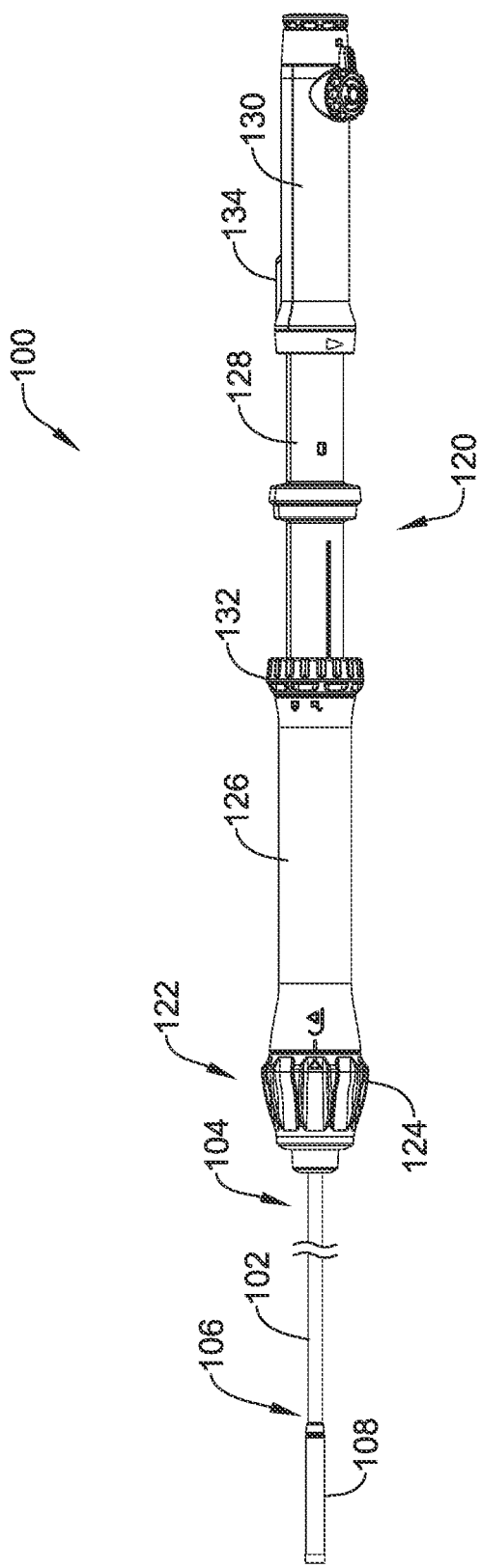
FIG. 3 is a plan view of an example delivery device for an implantable leadless cardiac pacing device.

FIG. 3 is a plan view of an illustrative delivery device 100, such as a catheter, that may be used to deliver the implantable device 10. The delivery device 100 may include an outer tubular member 102 having a proximal section 104 and a distal section 106. An intermediate tubular member 110 may be longitudinally slidably disposed within a lumen 150 of the outer tubular member 102 (see e.g., FIG. 4). An inner tubular member 116 may be longitudinally slidably disposed within a lumen 152 of the intermediate tubular member 110 (see e.g., FIG. 4). A distal holding section 108 may be attached to a distal end portion of the intermediate tubular member 110. In some cases, the distal holding section 108 may be tubular. The delivery device 100 may also include a handle assembly 120 positioned adjacent to the proximal section 104 of the outer tubular member 102. In some embodiments, the outer tubular member 102 may include at least a section thereof that has an outer diameter that is less than the outer diameter D1 of at least a portion of the holding section 108 (see e.g., FIG. 4).

Figure 4:
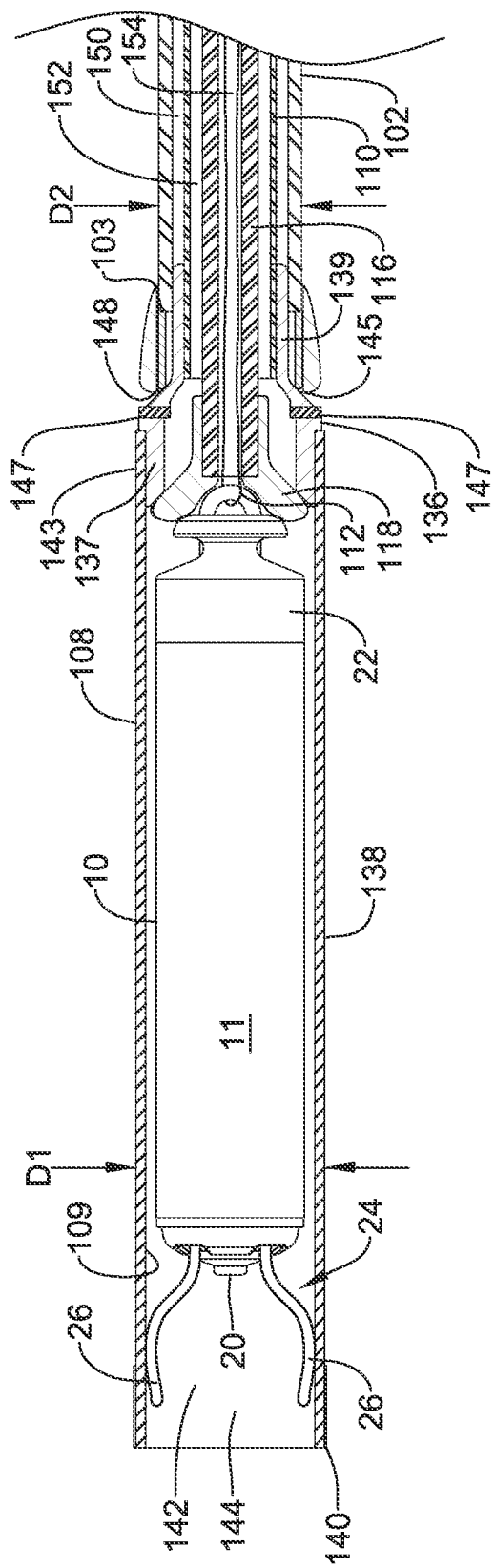
FIG. 4 is a partial cross-sectional side view of the distal portion of the delivery device of FIG. 3.

The handle assembly 120 may include a first or distal hub portion 126 attached to, such as fixedly attached to, the proximal end section 104 of the outer tubular member 102, a second or intermediate hub portion 128 attached to, such as fixedly attached to, a proximal end section of the intermediate tubular member 110, and a third or proximal hub portion 130 attached to, such as fixedly attached to, a proximal end section of the inner tubular member 116 (see e.g., FIG. 4). The first hub portion 126, second hub portion 128, and third hub portion 130 may be positioned in a generally telescoping arrangement and longitudinally slidable relative to each other. As will be discussed in more detail below, each of the first hub portion 126, the second hub portion 128, and the third hub portion 130 may be longitudinally slidable and rotatable relative to each other such that the outer tubular member 102, intermediate tubular member 110, and inner tubular member 116 may be individually actuated. In some instances, it may be desirable to move the outer tubular member 102, intermediate tubular member 110 and inner tubular member 116 simultaneously. The handle assembly 120 may include a multi-stage deployment mechanism or a first locking mechanism 134 to releasably couple the second hub portion 128 to the third hub portion 130 to prevent relative longitudinal movement therebetween, and thus prevent relative longitudinal movement between the intermediate tubular member 110 and the inner tubular member 116, as will be discussed in more detail below. The handle assembly 120 may also include a second locking mechanism 132 to releasably couple the first hub portion 126 to the second hub portion 128 to prevent relative longitudinal movement therebetween, and thus prevent relative longitudinal movement between the outer tubular member 102 and the intermediate tubular member 110, as will be discussed in more detail below.

The distal holding section 108 (e.g., a tubular distal holding structure) may be configured to receive the implantable device 10 therein. For example, referring to FIG. 4, which illustrates a partial cross-sectional view of a distal portion of delivery device 100, the holding section 108 may define a cavity 142 for slidably receiving the implantable device 10, and may include a distal opening 144 for slidable insertion and/or extraction of the implantable device 10 into and/or out of the cavity 142.

The distal holding section 108 may include a body portion 138 (e.g., a sleeve) and a distal tip portion 140 that may be, for example, configured to be atraumatic to anatomy, such as a bumper tip. For example, as the catheter is navigated through the anatomy, the distal tip may come into contact with anatomy. Additionally, when the catheter is used to deliver the device, the tip 140 of the delivery device 100 may come into contact with tissue adjacent the target site (e.g. cardiac tissue of the heart). A hard distal tip formed of the material of the outer tubular member 102 and/or intermediate tubular member 110 may injure a vessel wall or cardiac tissue. As such, it may be desirable to provide the delivery device 100 with a softer distal tip 140 that can be introduced into the anatomy and come into contact with anatomy adjacent the target cite without causing unnecessary trauma.

For example, the distal tip 140 may be made of a material that is softer than the body portion 138 of the distal holding section 108. In some cases, the distal tip 140 may include a material that has a durometer that is less than the durometer of the material of the body portion 138. In some particular embodiments, the durometer of the material used in the distal tip 140 may be in the range of about 5 D to about 70 D, or for example, in the range of about 25 D to about 65 D. Additionally, the distal tip 140 may include a shape or structure that may make it less traumatic to tissue. For example, the distal tip 140 may have a distal surface, such as a tissue contacting surface, that is rounded or includes a curvature configured to be more atraumatic to tissue.

In some embodiments, all or a portion of the distal holding section 108 may include an inner surface 109 that may be configured to resist getting caught on the fixation mechanism 24, such as the one or more of hooks or tines 26 on the device 10, and an exterior surface 11 (e.g., an outer surface) of the device 10. For example, the distal holding section 108 may include an inner layer or coating of harder or more lubricious material that resists force applied by the fixation mechanism 24 onto the inner surface of the distal holding section 108. For example, the distal holding section 108 may include a multi-layered structure, and an inner layer may be made of a material that is harder than an outer layer.

The inner tubular member 116 may be disposed (e.g., slidably disposed) within a lumen 152 of the intermediate tubular member 110. The inner tubular member 116 may be engaged by a user near or at the third hub portion 130, and extend through a lumen 152 of the intermediate tubular member 110 and into the distal holding section 108. A distal portion 118 of the inner tubular member 116 may be capable of engaging the device 10, and the inner tubular member 116 may be used to "push" the device 10 out from distal holding section 108 so as to deploy and anchor implantable device 10 within a target region (e.g., a region of the heart such as the right ventricle). The inner tubular member 116 may have a lumen 154 extending from a proximal end to a distal portion 118 thereof. A tether 112 or other retaining feature may be used to releasably secure the device 10 to the delivery device 100. In some instances, the tether 112 may be a single or unitary length of material that may extend from a proximal end of the lumen 154, out through the distal portion 118, through the opening 38 of the device 10 and return to the proximal end of the inner tubular member 116 through the lumen 154 such that both ends of the tether 112 are positioned adjacent to the third hub portion 130. In some instances, as will be discussed in more detail below, the ends of the tether 112 may be secured within a locking feature in the third hub portion 130.

In order to more specifically place or steer the delivery device 100 to a position adjacent to the intended target, the delivery device 100 may be configured to be deflectable or articulable or steerable. Referring to FIG. 3, for example, the outer tubular member 102 and/or intermediate tubular member 110 may include one or more articulation or deflection mechanism(s) that may allow for the delivery device 100, or portions thereof, to be deflected, articulated, steered and/or controlled in a desired manner. For example, the outer tubular member 102 may include at least a portion thereof that can be selectively bent and/or deflected in a desired or predetermined direction. This may, for example, allow a user to orient the delivery device 100 such that the holding section 108 is in a desirable position or orientation for navigation or delivery of the device 10 to a target location. The outer tubular member 102 may be deflected, for example, along a deflection region.

A wide variety of deflection mechanisms may be used. In some example embodiments, deflection may be effected by one or more actuation members, such as pull wire(s) extending between a distal portion of the outer tubular member 102 and an actuation mechanism 122 near the proximal end of the outer tubular member 102. As such, the one or more pull wires may extend both proximally and distally of the desired deflection or bending region or point. This allows a user to actuate (e.g., "pull") one or more of the pull wires to apply a compression and/or deflection force to at least a portion of the outer tubular member 102 and thereby deflect or bend the outer tubular member 102 in a desired manner. In addition, in some cases the one or more wires may be stiff enough so that they can also be used to provide a pushing and/or tensioning force on the outer tubular member 102, for example, to "push" or "straighten" the shaft into a desired position or orientation.

In some embodiments, the actuation member takes the form of a continuous wire that is looped through or otherwise coupled to a distal end region of the outer tubular member 102 so as to define a pair of wire sections. Other embodiments are contemplated, however, including embodiments where the actuation member includes one or a plurality of individual wires that are attached, for example, to a metal or metal alloy ring adjacent the distal end region of the outer tubular member 102.

The actuation mechanism 122 may include a desired mechanism that may allow for applying tension (i.e. pulling force), or compression (i.e. pushing force), or both, on the actuation member(s). In some embodiments, the actuation mechanism 122 may include an external rotatable member 124 connected to and rotatable about the longitudinal axis of the handle assembly 120. The rotatable member 124 may threadingly engage an internal member that is attached to the proximal end of the actuation member(s) or pull wires. When the external rotatable member 124 is rotated in a first rotational direction, the internal member translates in a first longitudinal direction, thereby applying tension to the pull wire(s), which applies compression force to the shaft, so as to deflect the outer tubular member 102 from an initial position to a deflected position. When the external rotatable member 124 is rotated in a second rotational direction, the internal member translates in a second longitudinal direction, thereby reducing and/or releasing the tension on the pull wire(s), and allowing the outer tubular member 102 to relax back toward the initial position. Additionally, in some cases, as mentioned above, where the one or more wires may be stiff enough, rotation of the rotatable member 124 in the second rotational direction such that the internal member translates in a second longitudinal direction may apply compression to the wire(s), such that the wire(s) may apply tension to the outer tubular member 102 and "push" the outer tubular member 102 back toward an initial position, and possibly into additional positions beyond the initial position.

The one or more articulation and/or deflection mechanism(s) may also entail the outer tubular member 102 including structure and/or material that may provide for the desired degree and/or location of the deflection when the compressive or tensile forces are applied. For example, the outer tubular member 102 may include one or more sections that include structure and/or material configured to allow the shaft to bend and/or deflect in a certain way when a certain predetermined compressive and/or tensile force is applied. For example, the shaft may include one or more sections that are more flexible than other sections, thereby defining a bending or articulating region or location. Some such regions may include a number of varying or changing flexibility characteristics that may define certain bending shapes when predetermined forces are applied. Such characteristics may be achieved through the selection of materials or structure for different sections of the outer tubular member 102.

In other embodiments, other articulation and/or deflection mechanism(s) are contemplated. For example, all or a portion of the delivery device 100, such as the outer tubular member 102, may be made of a shape memory material, such as a shape memory polymer and/or a shape memory metal. Such materials, when stimulated by an actuation mechanism, such as a change in temperature or the application of an electrical current, may change or move from a first shape to a second shape. As such, these material and mechanism may be used to deflect or bend the outer tubular member 102 in a desired manner. Other suitable deflection mechanism(s) that are able to deflect the delivery device 100 may also be used. Such alternative mechanisms may be applied to all other embodiments shown and/or discussed herein, and others, as appropriate.

Furthermore, the outer tubular member 102 may include one or more predefined or fixed curved portion(s) along the length thereof. In some cases, such curved sections may be configured to fit with particular anatomies or be configured for better navigation or delivery of the device 10. Additionally, or alternatively, some such curved sections may be configured to allow the outer tubular member 102 to be predisposed to be bent and/or deflected in a certain direction or configuration when compression and/or tension forces are applied thereto. It is contemplated that the outer tubular member 102 may be a laser cut metallic tubing, a braid reinforced polymeric tubing, or other flexible tubular structure as desired.

Returning again to FIG. 4, the distal holding section 108 may be affixed to a distal end portion of the intermediate tubular member 110. The distal holding section 108 may include a hub portion 136 and a tubular body portion 138. In some instances, a proximal region 143 of the body portion 138 may be heat bonded to a distal end portion 137 of the hub portion 136, or otherwise affixed. The hub portion 136 may include a tapered intermediate region 145 disposed between a proximal end portion 139 and the distal end portion 137.

In some instances, the hub portion 136 may be formed from a metal or metal alloy while the body portion 138 may be formed from a polymeric material, although this is not required. Alternatively, or in addition, the hub portion 136 be formed from a polymeric material with a metal or metal alloy insert.

One or more electrical ports 147 may be located in the distal holding section 108, such as at a location proximal of the proximal end of the implantable device 10 when the implantable device 10 is positioned within the distal holding section 108 (e.g., within a cavity of the distal holding section 108). In some cases, metal or metal alloy of the distal hub portion 136 may form the electrical ports 147 and allow electrical signals (e.g., current) to pass from interior the distal holding section 108 to exterior the distal holding section 108. Additionally, or alternatively, the electrical ports 147 may be located along the body portion 138 of the distal holding section 108, at a location adjacent to and/or proximal of the second electrode 22 (e.g., adjacent to and/or proximal of the proximal end 14 of the leadless device 10).

In some embodiments, the outer tubular member 102 may include a metal ring or tip adjacent the distal end 103 thereof for attaching one or more pull wires thereto. It is contemplated that the outer tubular member 102 may further include a lubricious liner, such as, but not limited to a polytetrafluoroethylene (PTFE) liner. The proximal end portion 139 of the hub portion 136 may extend proximally into the lumen 150 of the outer tubular member 102. In some instances, an outer surface of the proximal end portion 139 may form an interference fit with an inner surface of the outer tubular member 102. It is contemplated that the outer surface of the proximal end portion 139 and the inner surface of the outer tubular member 102 may engage and/or may be coupled in a tapered engagement. For example, the distal end 103 of the outer tubular member 102 may flare radially outwards in the distal direction and/or the proximal end portion 139 may taper radially inward in the proximal direction. The two angled surface may engage as the proximal end portion 139 is proximally retracted within the outer tubular member 102. Other coupling arrangements may be used as desired.

It is contemplated that as the outer tubular member 102 is bent to navigate the implantable device 10 to the desired location, the proximal end portion 139 may advance distally and disengage from the inner surface of the outer tubular member 102 creating a kink point or weakened region adjacent to the bonding region 146. Proximally retracting the intermediate tubular member 110 to bring the intermediate region 145 into contact with the outer tubular member 102 at contact point 148 and/or bringing the proximal end portion 139 into the outer tubular member 102 and fixing the intermediate tubular member 110 in this configuration may help prevent migration of the distal holding section 108 during navigation of the delivery device 100 to the desired location. Such a configuration may also place the intermediate tubular member 110 in tension while the distal holding section 108 applies a compression force on the outer tubular member 102, as will be discussed in more detail below. As discussed above, a locking mechanism 132 in the handle assembly 120 may be utilized to releasably maintain the outer tubular member 102 and the intermediate tubular member 110 in a desired orientation.

Figure 5:
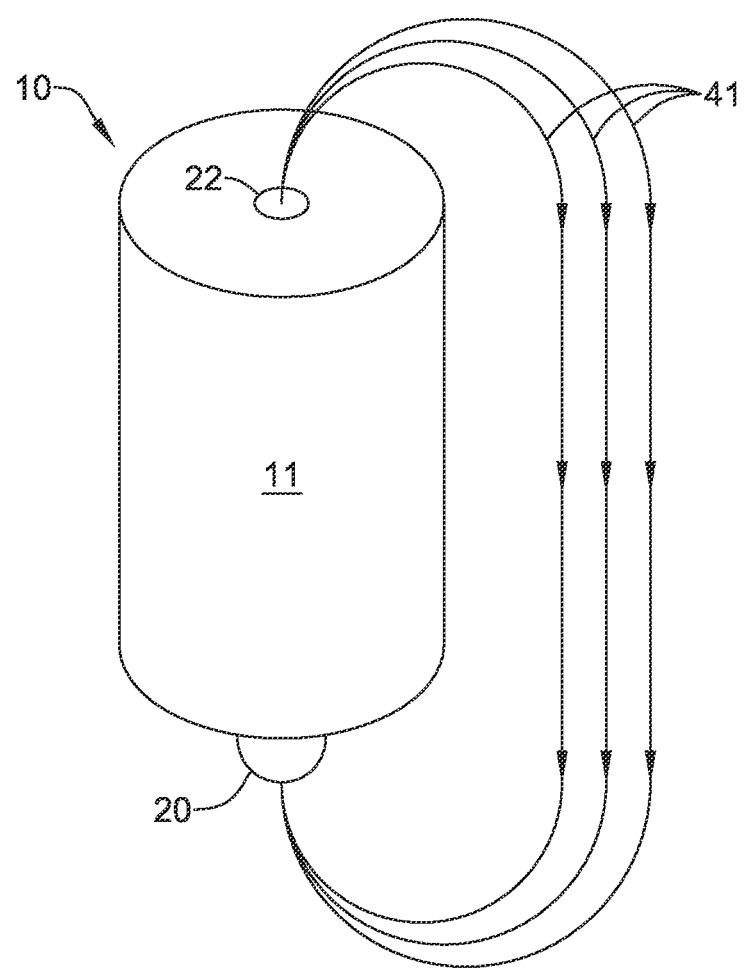
FIG. 5 is a perspective view of an example schematic implantable leadless cardiac pacemaker deploying field lines.
Figure 6:
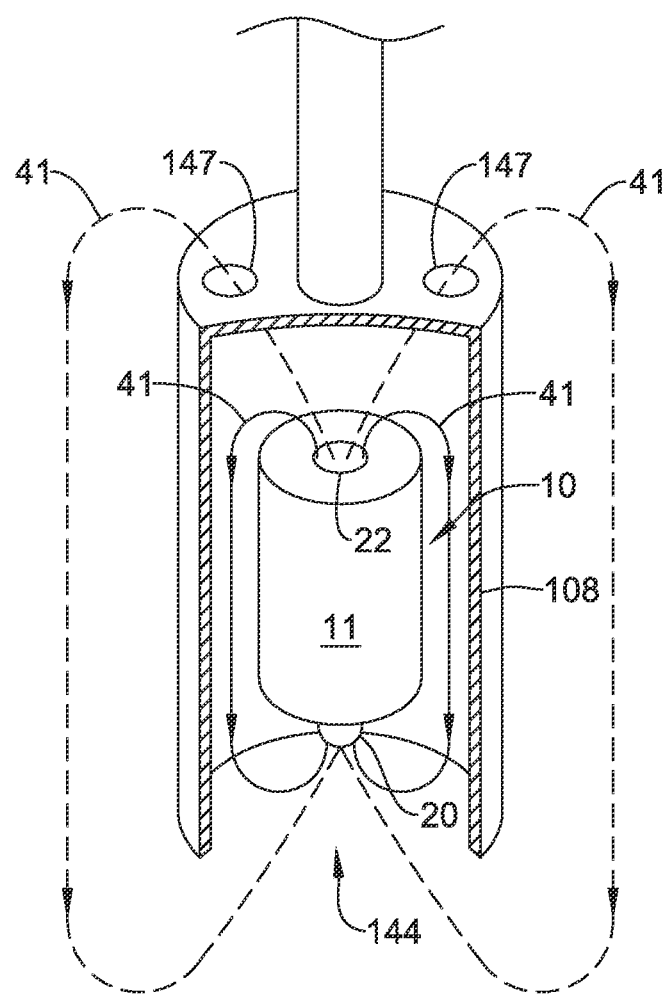
FIG. 6 is a perspective partial cross-sectional view of an example schematic implantable leadless cardiac pacemaker in a holding chamber of a delivery device, where the implantable leadless cardiac pacemaker is deploying field lines.
Figure 7:
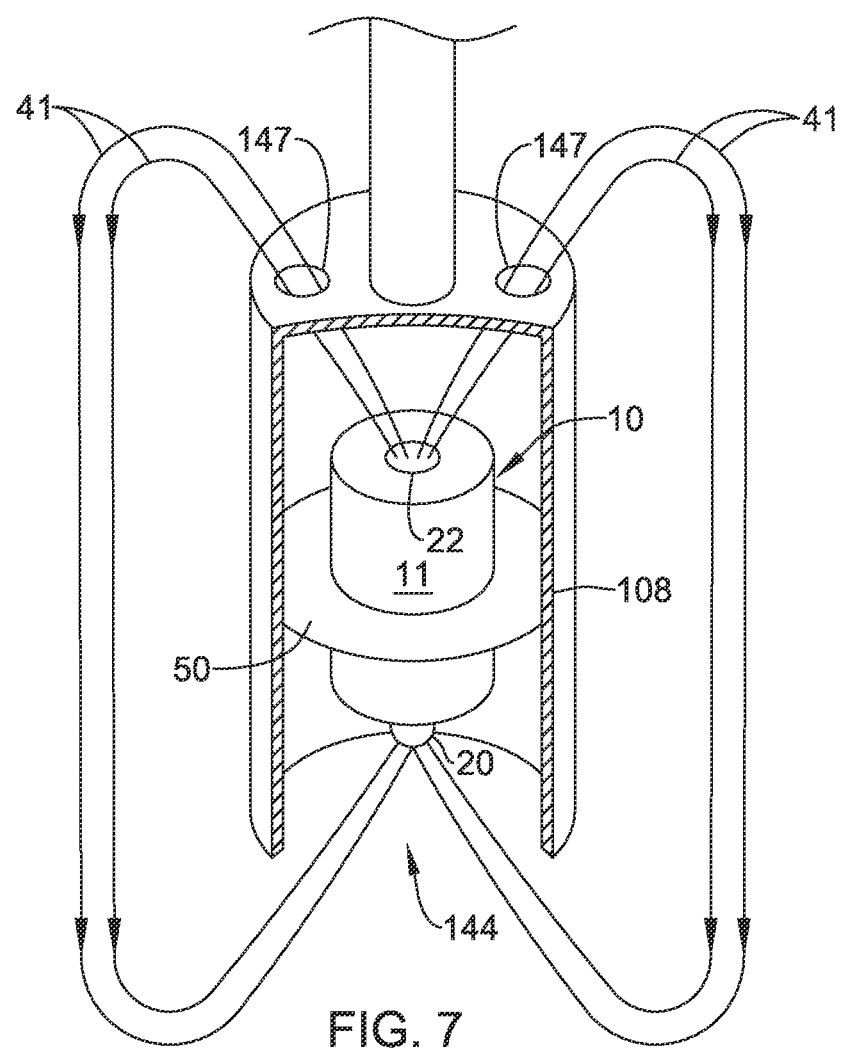
FIG. 7 is a perspective partial cross-sectional view of an example schematic implantable leadless cardiac pacemaker in a holder chamber of a delivery device, where the implantable leadless cardiac pacemaker is deploying field lines and a barrier inhibits field lines within the sleeve.

FIGS. 5-7 depict electrical field lines 41 (e.g., lines depicting a flow of electrical current) deployed from the implantable device 10 and show examples of how the deployed field lines 41 may be directed while the leadless pacemaker is positioned within the distal holding section 108. Although certain configurations for directing field lines are depicted in different Figures, some or all of the configurations may be used together and the contemplated configurations are not limited to those depicted in the Figures.

FIG. 5 depicts a schematic implantable device 10. The implantable device 10 may include a first or distal electrode 20 at or near a distal end 16 of the device 10 and a second or proximal electrode 22 at or near a proximal end 14, with the distal electrode 20 located distal of the proximal electrode 22. Field lines 41, as shown in FIG. 5, depict current traveling from the second electrode 22 to the first electrode 20. When the implantable device 10 is implanted in a patient, the current deployed from the implantable device 10, as by field lines 41, may be applied to a patient (e.g., a patient's heart) to provide therapy and/or produce communication. Additionally or alternatively, field lines 41 may be utilized to sense one or more characteristics of the heart or tissue around the implantable device 10.

Typically, current distribution from the implantable device 10 may be symmetrical and an external voltage field may be proportional to a dipole current and a dipole length between the first electrode 20 and the second electrode 22. The dipole length is a distance a current travels between the first electrode 20 and the second electrode 22.

In some cases, prior to deployment of the implantable device 10 from the distal holding section 108 or otherwise while the leadless pacemaker is within a sleeve of a delivery device, it may be desirable to communicate with the implantable device 10. Such communication may allow for assessment of device status prior to releasing the fixation mechanisms into a patient (e.g., into a patient's myocardium) and/or deploying the device 10 from the distal holding section 108. Although the distal holding section 108 may include one or more electrical ports 147 adjacent a proximal end portion 139 of the distal holding section 108 to facilitate communicating with the leadless pacemaker while it is within the distal holding section 108, signal losses and communication impairment may be observed. Such signal losses and/or communication impairment may be due, at least in part, to current crowding inside the distal holding section 108.

FIG. 6 depicts a schematic view of an implantable device 10 located within the distal holding section 108 of a delivery device 100, where the distal holding section 108 is pictured in cross-section. Although some of the field lines 41 depicting current deployed from the implantable device 10 are shown in FIG. 6 as passing through electrical ports 147 to an exterior of the distal holding section and back in through the distal opening 144 to the first electrode 20, a portion of the current deployed from the implantable device 10 remains within the distal holding section 108 and passes directly to the first electrode 20 without exiting the distal holding section 108. A portion of the current deployed from the implantable device 10 may remain within the distal holding section 108 because the current finds the least resistive path from the second electrode 22 (e.g., an anode) to the first electrode 20 (e.g., a cathode) and in some cases, it may be easier for a portion of the current to remain within the distal holding section 108 despite the electrical ports 147. That is, there may be reduced current density from current deployed by the implantable device 10 external the distal holding section 108, but the current external the distal holding section 108 may result in a longer dipole length which may be advantageous for increasing a voltage field. Because only a portion of the current of the implantable device 10 exits the distal holding section 108, a strength of a communication signal with the implantable device 10 may be impaired.

FIG. 7 depicts a schematic of an implantable device 10 located within the distal holding section 108 of the delivery device 100, where an electrically insulative (i.e., dielectric) barrier 50 may be positioned between a first end (e.g., a proximal end 14) and a second end (e.g., a distal end 16) of the implantable device 10 such that the first electrode 20 is located distal of the electrically insulative barrier 50 and the second electrode 22 is located proximal of the electrically insulative barrier 50. The barrier 50 may entirely circumferentially fill or at least partially fill a radial space between an exterior surface 11 of the implantable device 10 and an inner surface 109 of the distal holding section 108. The barrier 50 may impair current travel between the first end and the second end of the implantable device 10 (e.g., between the second electrode 22 and the first electrode 20) within the distal holding section 108. As a result, current travel within in the distal holding section 108 may be eliminated, substantially eliminated, or reduced and the current deployed from the second electrode 22 of the implantable device 10 may be forced to exit the distal holding section 108 via the electrical ports 147 to travel to the first electrode 20 via an electrical current path external of the distal holding section 108 (e.g., the path of least electrical resistance may be from the second electrode 22 through the electrical ports 147, to tissue and/or blood external of the distal holding section 108, and back in the distal opening 144 to the first electrode 20. Such a configuration of the electrically insulative barrier 50, the implantable device 10, and the distal holding section 108 may result in a full or substantially full strength current density with a long dipole length (e.g., longer than when the current is not required to travel through the electrical ports 147 and along a path exterior of the distal holding section 108). Because all or substantially all of the current of the implantable device 10 exits the distal holding section 108 via electrical ports 147 and a length of travel of the current is longer when the current exits the distal holding section 108, a strength of a communication signal with the implantable device 10 may be strong relative to when a barrier 50 is not present.

Figure 8:
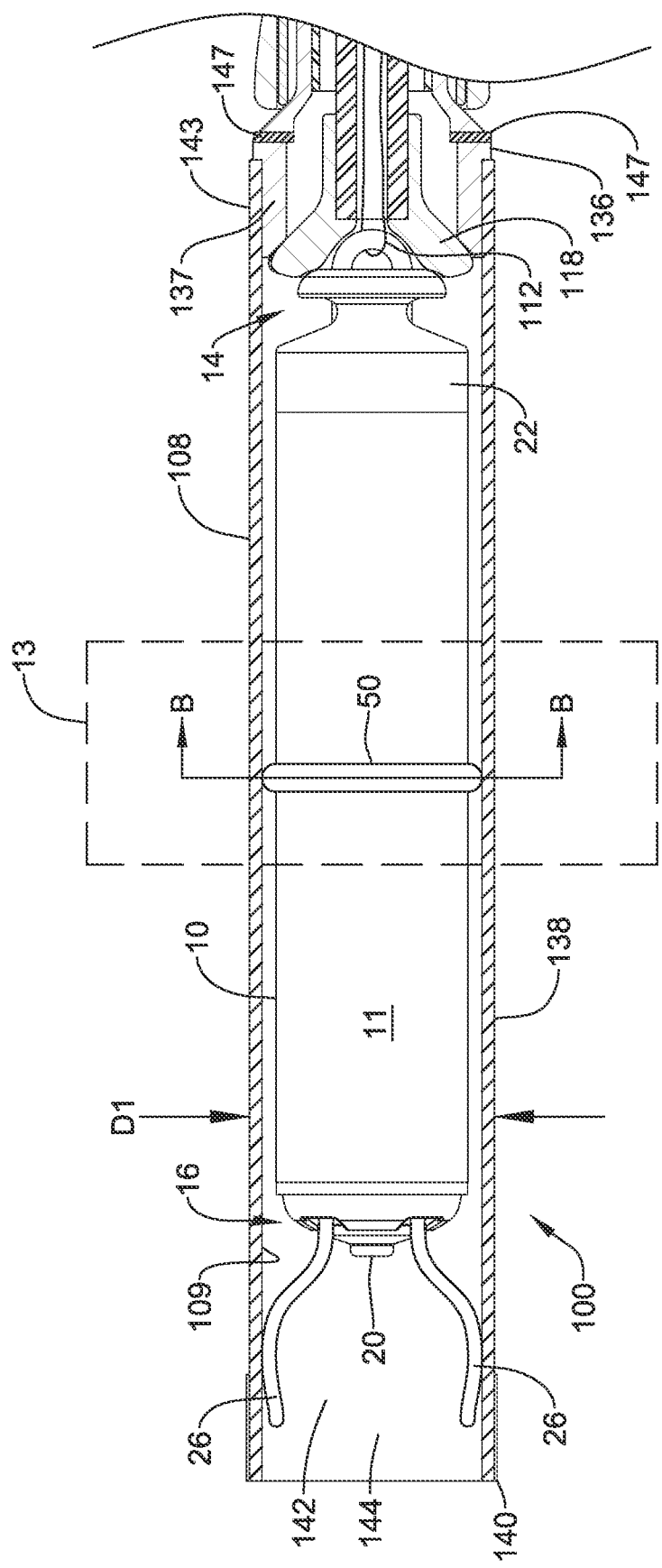
FIG. 8 is a partial cross-sectional side view of a distal portion of an example delivery device for an implantable leadless cardiac pacing device, where an illustrative barrier is positioned between a first end and a second end of the implantable leadless cardiac pacing device.

FIG. 8 a partial cross-sectional view with a distal holding section 108 of a delivery device 100 in cross-section and a side view of the implantable device 10 within the distal holding section 108 of the delivery device 100. As seen in FIG. 8, a side view of an electrically insulative barrier 50 is depicted, where the barrier 50 (e.g., where the barrier 50 is shown in schematic form) may circumferentially extend around the circumference of the implantable device 10 and extend radially between the exterior surface 11 of the implantable device 10 and the inner surface 109 of the distal holding section 108. The barrier 50 depicted in FIG. 8 may be a ring extending circumferentially around the implantable device 10 to block electrical signals (e.g., current) from traveling between the proximal end 14 and the distal end 16 of the implantable device 10.

FIGS. 9-14 depict various illustrative configurations of the barrier 50. These illustrative configurations of the barrier 50, along with others, may be usable individually and/or together to form the barrier 50.

The electrically insulative barrier 50 may take on any form that inhibits or prevents current (e.g., electrical signals) from traveling within the distal holding section 108 between the second electrode 22 (e.g., at a proximal end of the implantable device 10) and the first electrode 20 (e.g., at a distal end of the implantable device 10) of the implantable device 10. The barrier 50 may be part of, affixed to, and/or extend from the implantable device 10, the distal holding section 108, or both of the implantable device 10 and the distal holding section 108. Examples of barriers 50 may include, but are not limited to, o-rings, lip seals, tapered sleeves, curved leadless pacemakers, annular ridges or rims, polymer bands, nonconductive gel fillers, silicon molded features, burpable seals, internally sprung sleeves with a nitinol waist, and/or other dielectric barriers configured to inhibit the travel of electrical current, any of which may circumferentially extend around the exterior of the implantable device 10 and/or the interior of the distal holding section 108.

Figure 9:
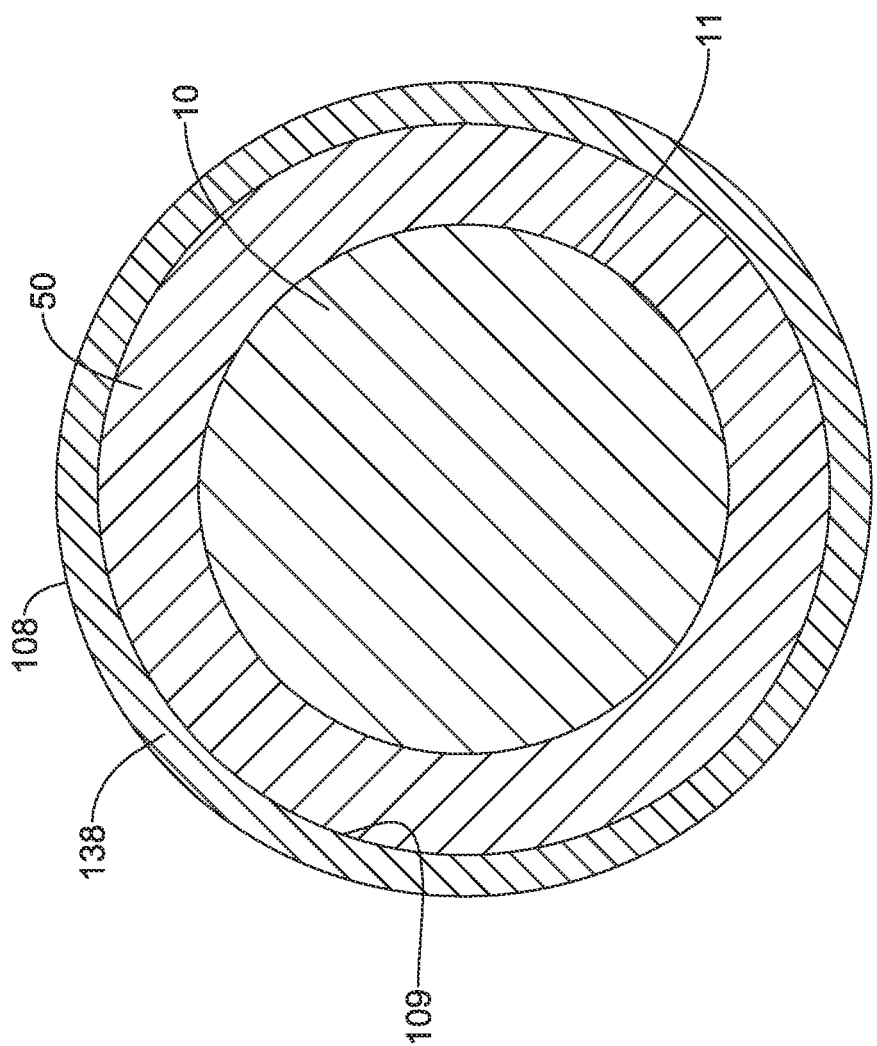
FIG. 9 is a cross-sectional view of the distal portion of the delivery device of FIG. 8, taken along line B-B showing an example configuration of the barrier positioned between the first end and the second end of the implantable leadless cardiac pacing device.
Figure 10:
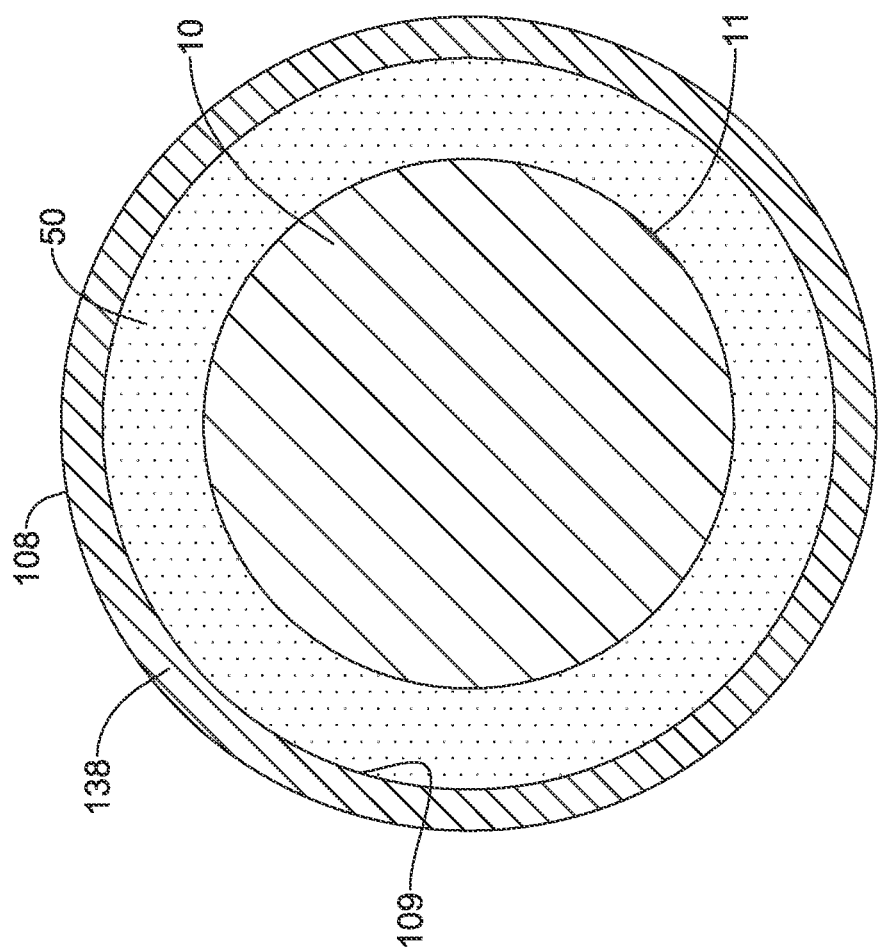
FIG. 10 is a cross-sectional view of the distal portion of the delivery device of FIG. 8, taken along line B-B showing an example configuration of the barrier positioned between the first end and the second end of the implantable leadless cardiac pacing device.

FIGS. 9-11 are cross-sectional views taken along line B-B in FIG. 8, which depict various illustrative configurations of the barrier 50 having a general ring-shape. FIG. 9 depicts an O-ring configuration. The o-ring configuration of the barrier 50 in FIG. 9 may extend between an exterior surface 11 of the implantable device 10 and the inner surface 109 of the body portion 138 of the distal holding section 108. The o-ring may be attached to one or more of the implantable device 10 and the body portion 138 at a location that is between the proximal end 14 and the distal end 16 of the implantable device 10 when the implantable device 10 is within the distal holding section 108 of the delivery device 100. Alternatively, the o-ring barrier may be unattached and instead, engage one or more of the implantable device 10 and the body portion 138 through a friction fit or other engagement.

FIG. 10 depicts a ring-shaped barrier 50 having an o-ring configuration filled with a gel. The gel in the barrier 50 of FIG. 10 is represented by dots between the implantable device 10 and the body portion 138. In some cases, the gel may be a nonconductive gel filler configured to prevent an electrical signal from crossing between a proximal side of the barrier 50 and a distal side of the barrier 50. The gel-filled configuration of barrier 50 may completely fill or at least partially fill a radial space between an exterior surface 11 of the implantable device 10 and an inner surface 109 of the distal holding section 108. In one example, the gel-filled configuration of barrier 50 may extend between an exterior surface 11 of the implantable device 10 and the inner surface 109 of the body portion 138 of the distal holding section 108. The gel filled barrier 50 may be attached to one or more of the implantable device 10 and the body portion 138 at a location that is between the proximal end 14 and the distal end 16 of the implantable device 10 when the implantable device 10 is within the distal holding section 108 of the delivery device 100. Alternatively, the gel filled barrier may be unattached and instead, engage one or more of the implantable device 10 and the body portion 138 through a friction fit or other engagement.

Figure 11A:
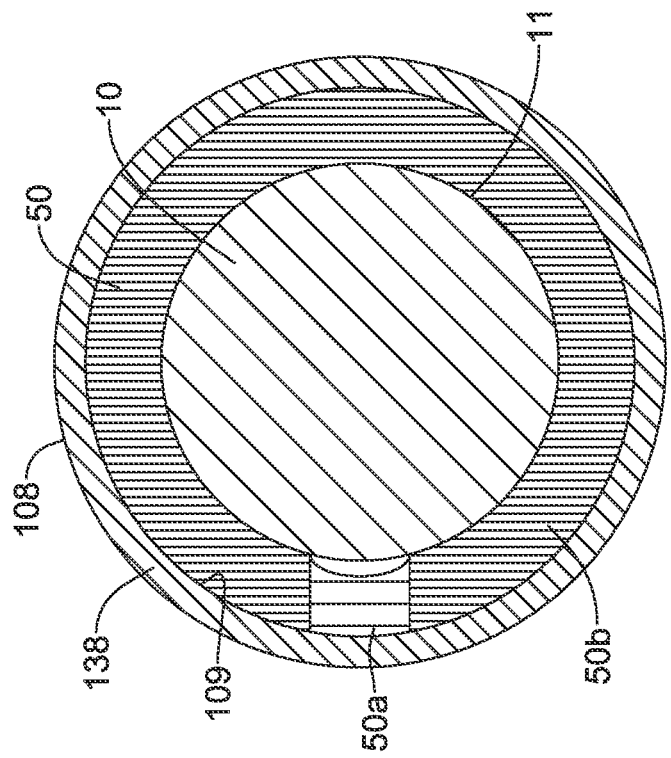
FIGS. 11A and 11B are cross-sectional views of the distal portion of the delivery device of FIG. 8, taken along line B-B showing an example configuration of the barrier positioned between the first end and the second end of the implantable leadless cardiac pacing device.
Figure 11B:
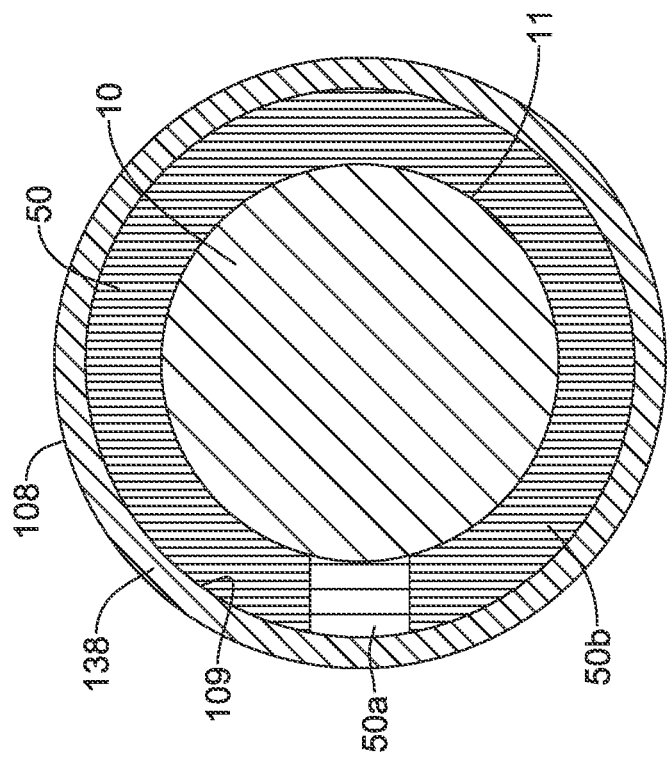

In some cases, a fluid (e.g., saline or other fluid) may be provided through the delivery device 100 to a cavity 142 (e.g., at least partially defined by the body portion 138) of the distal holding section 108, such as to flush the system. In such instances and others, a barrier 50 may be utilized that allows fluid to pass from a proximal side to a distal side of the barrier 50 such that the fluid may pass from a portion of the cavity 142 of distal holding section 108 proximal of the barrier 50 to a portion of the cavity of the distal holding section 108 distal of the barrier 50, but prevent electrical current from so passing when the fluid is not crossing the barrier 50. In one example, shown in FIG. 11A, the barrier 50 may have one or more portions having a first tension and one or more portions having a second tension, where the first tension may be less than the second tension. Illustratively, the barrier 50 may have a first portion 50a having a first tension and/or stiffness that is less than a second tension and/or stiffness of a second portion 50b, where the first portion 50a and the second portion 50b work together to prevent electrical current from traveling between the proximal end 14 and the distal end 16 of the implantable device 10 within the distal holding section 108. With such a barrier 50, as shown in FIG. 11B, the first portion 50a may flex or deform in response to a pressure greater than a threshold pressure that may be less than that required to flex or deform the second portion 50b to allow fluid to pass through the first portion 50a. Once the pressure is no longer at or above the threshold pressure (i.e., when the pressure is below the threshold pressure, the first portion 50a may return to its biased position and may work with the second portion 50b form a circumferential electrically insulative seal around the device 10 to prevent electrical current from crossing within the distal holding section 108 between the second electrode 22 at the proximal end 14 and the first electrode 20 at the distal end 16 of the implantable device 10.

The first portion 50a and the second portion 50b of the barrier 50 may be made of any electrically insulative material configured to inhibit electrical signals and may be made from the same or different material. In instances when the first portion 50a and the second portion 50b are made from the same or similar materials, other materials may be added to one or more of the first portion 50a and the second portion 50b be to ensure the first portion 50a has a tension or stiffness that is less than a tension or stiffness of the second portion 50b.

The first portion 50a and/or the second portion 50b may be attached to one or more of the implantable device 10 and the body portion 138 at a location that is between the proximal electrode 22 and the distal electrode 20 of the implantable device 10 when the implantable device 10 is within the distal holding section 108 of the delivery device 100. Alternatively, or in addition, the first portion 50a and/or the second portion 50b may be unattached and instead, engage one or more of the implantable device 10 and the body portion 138 through a friction fit or other engagement.

The first portion 50a and the second portion 50b of the barrier 50 may have any size relative to one another. In one example, the first portion 50a and the second portion 50b may have the same radial width dimensions, but different circumferential dimensions. However, this is not required and the first portion 50a and the second portion 50b may have different radial width dimensions and/or the same circumferential dimensions. In the example depicted in FIGS. 11A and 11B, the first portion 50a of the barrier 50 has a same radial width dimension as a radial width dimension of the second portion 50b of the barrier 50, but the first portion 50a has a smaller circumferential dimension than the second portion 50b. Additionally, although only a single first portion and a single second portion 50b are depicted in FIGS. 11A and 11B, two or more first portions 50a and/or two or more second portions 50b may be circumferentially and/or radially spaced to form the barrier 50 preventing electrical current from passing between the proximal end 14 and the distal end 16 of the implantable device 10 (e.g., crosses an axial location of the barrier 50) within the distal holding section 108.

Figure 12B:
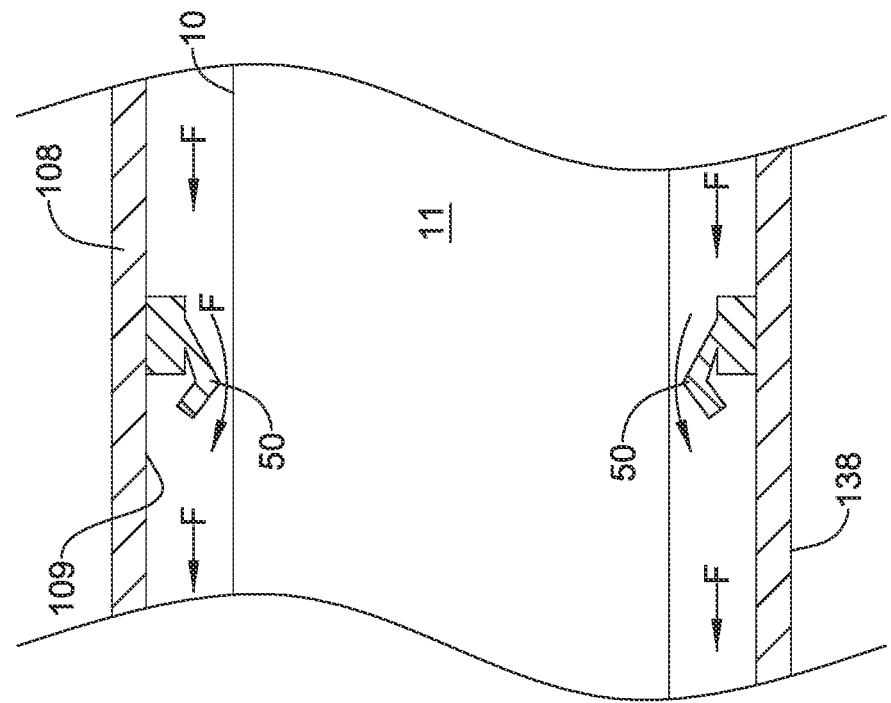
FIGS. 12A and 12B are partial cross-sectional side views of a distal portion of an example delivery device for an implantable leadless cardiac pacing device, where an illustrative barrier is positioned between a first end and a second end of the implantable leadless cardiac pacing device.
Figure 12A:
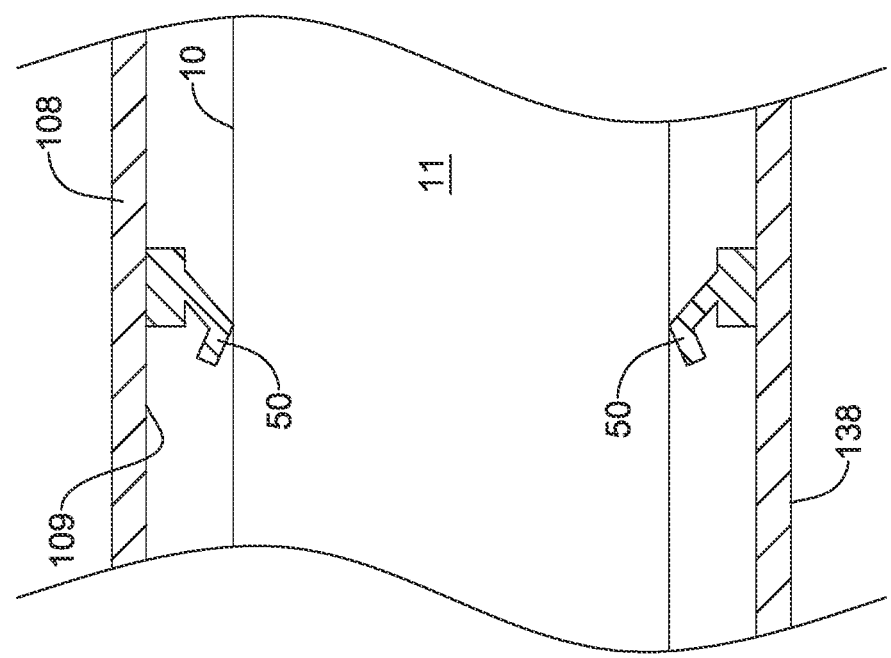

FIGS. 12A and 12B are partial cross-sectional views taken from dashed box 13 in FIG. 8, depicting an illustrative distal holding section 108 and barrier 50 in cross-section about the implantable device 10. The barrier 50 in FIG. 12A may be a lip-seal. The lip-seal may be made from any of one or more materials, where at least one of the materials may be configured to inhibit electrical current.

The lip-seal may be attached to one or more of the implantable device 10 and the body portion 138 at a location that is between the proximal end 14 and the distal end 16 of the implantable device 10 when the implantable device 10 is within the distal holding section 108 of the delivery device 100. In one example, the lip-seal may be attached to the body portion 138 and have a lip that contacts the implantable device 10 to inhibit electrical current trying to pass within the distal holding section 108 between the second electrode 22 at the proximal end 14 and the first electrode 20 at the distal end 16 of the implantable device 10. In some cases, the lip seal may be biased toward the central axis of the implantable device 10 and may flex radially outward under pressure (e.g., when a pressure crosses a threshold), as shown in FIG. 12B, to allow a fluid F to cross the barrier 50 from a portion of the cavity 142 of distal holding section 108 proximal of the barrier 50 to a portion of the cavity of the distal holding section 108 distal of the barrier 50, but prevent electrical current from so passing when the fluid F is not crossing the barrier 50. In one example, the lip-seal may have a point contact with the implantable device 10, where a distal side of the point contact may have an angle with the exterior surface 11 of the implantable device 10 that is different than an angle of the proximal side of the point contact with respect to the exterior surface 11. Other configurations are contemplated.

Figure 13:
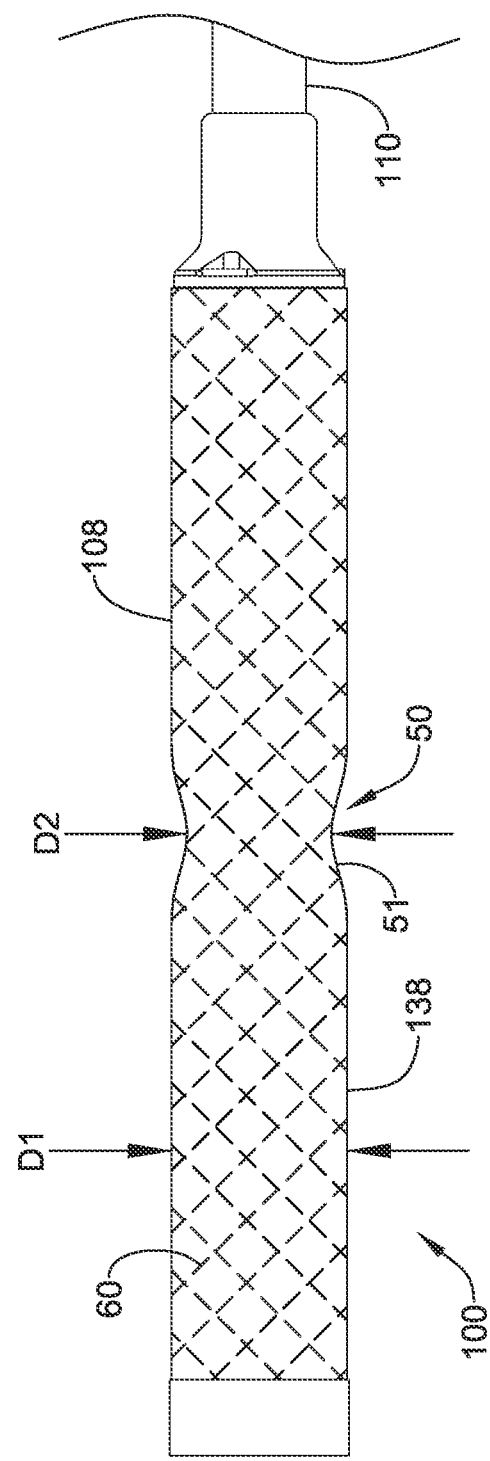
FIG. 13 is a plan view of an illustrative distal portion of a delivery device for an implantable leadless cardiac pacing device.
Figure 14:
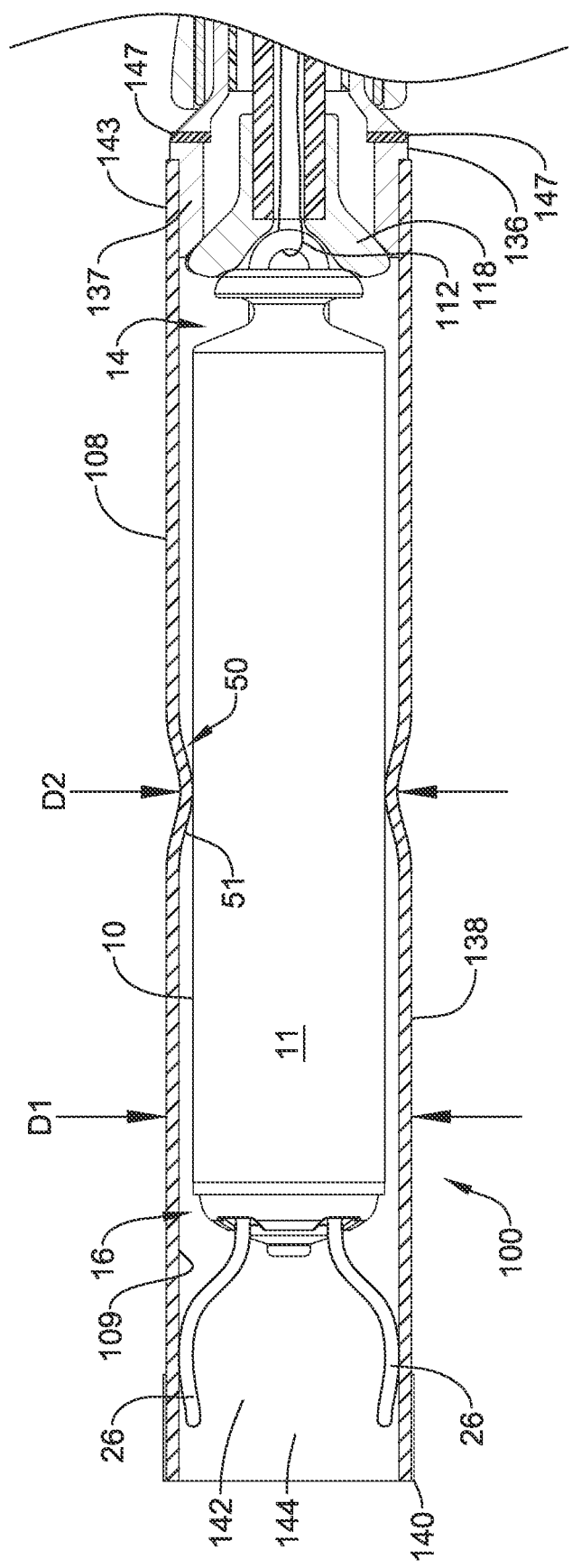
FIG. 14 is a partial cross-sectional side view of the distal portion of an example delivery device for an implantable leadless cardiac pacing device depicted in FIG. 13.

FIGS. 13 and 14 depict views of a body portion 138 of a distal holding section 108, where the body portion 138 may form or at least partially form a barrier 50. In some cases, the body portion 138 may include a reduced diameter portion 51 (e.g., tapered or necked down portion) forming the barrier 50, where the body portion 138 has a diameter D1 at an axial location distal of the reduced diameter portion 51 and the reduced diameter portion 51 has a diameter D2 that is less than the diameter D1. FIG. 13 is a side view of the distal holding section 108 having the reduced diameter portion 51 forming the barrier 50. FIG. 14 is a partial cross-sectional view showing the holding section 108 having the reduced diameter portion 51 forming the barrier 50 in cross-section and showing the implantable device 10 in a side view. As seen in FIG. 14, the reduced diameter portion 51 may taper toward a central axis of the body portion 138 and contact an implantable device 10 when the implantable device 10 is located within the distal holding section 108 to create a barrier 50 preventing electrical current from traveling between a proximal end 14 and a distal end 16 of the implantable device 10.

Braiding 60 is depicted in FIG. 13 by the dashed lines. This braiding 60 may be embedded or at least partially embedded in the material of the body portion 138 of the distal holding section 108. The braiding 60 may be configured to provide structural integrity to the body portion 138 and may be configured to taper or tighten (e.g., have a tightened portion) to form the barrier 50 in the material of the body portion 138. In some instances, the filaments of the braiding 60 may be positioned closer together (e.g., denser braiding) to form the barrier 50 than along other portions of the distal holding section 108. The braiding 60 may be formed of any material including, but not limited to, nickel, titanium, a nickel-titanium alloy (e.g., nitinol), polymer threads, or other material. If the braiding 60 is made from a material that may be considered a good conductor of electricity, the other material of the body portion 138 forming barrier 50 may be dielectric and may prevent electrical signals from passing between the second electrode 22 and the first electrode 20.

In some cases, the braiding 60 and the body portion 138 of the distal holding section 108 may be configured to flex or change shapes under tension or pressure greater than a threshold tension or pressure. In one example of when the braiding 60 is configured from a nickel-titanium alloy or other shape changeable material, the braiding 60 may be biased toward a central axis of the distal holding section 108 and when under pressure (e.g., from a fluid on the proximal side of the barrier 50), the braiding 60 may flex to relieve the pressure (e.g., flex to allow the fluid to pass to the distal side of the barrier 50) and then return to its shape forming the barrier 50 once a pressure proximal of the barrier 50 (e.g., a proximal pressure relative to a pressure distal of the barrier 50) falls below a threshold pressure.

Although not necessarily shown, an implantable device 10 may include a protrusion that engages the body portion 138 of the distal holding section 108 to form the barrier 50. The protrusion from the implantable device 10 may take the form of any and/or all of the barriers 50 discussed herein and may provide any and/or all of the functionality of the barriers 50 discussed herein.

Figure 15:
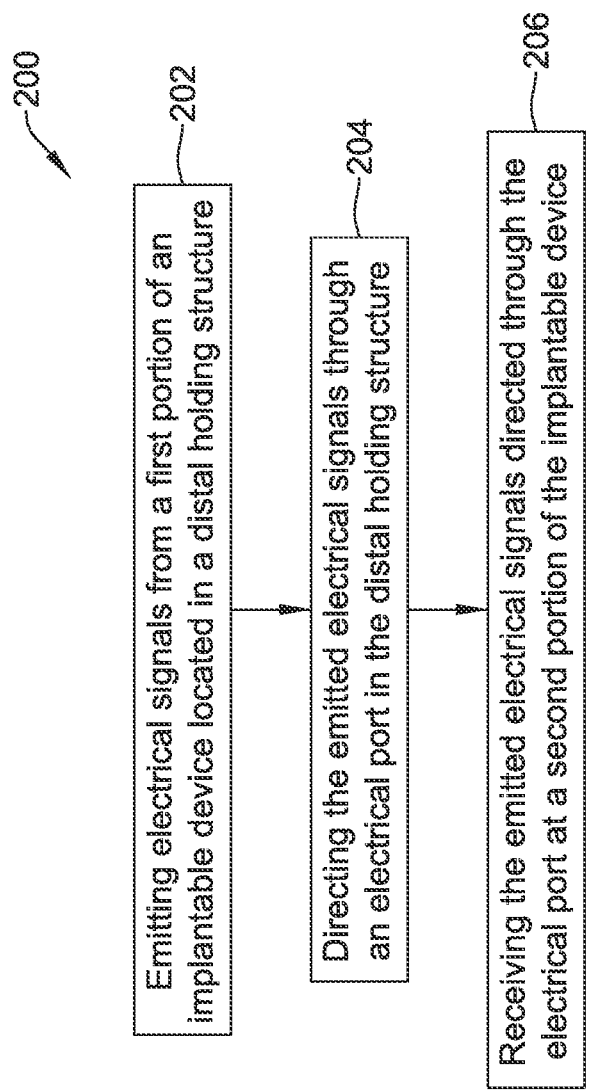
FIG. 15 is a schematic flow diagram of an illustrative method of directing electrical signals from an implantable device located within a holding structure.

The barrier 50 may be utilized in a method 200, for example as shown in FIG. 15, of directing electrical signals from an implantable device 10 (e.g., a leadless pacing device) received in a distal holding section 108 of a delivery device 100. The method 200 may include emitting 202 electrical signals from a second electrode 22 (e.g., a first portion) of the implantable device 10, while the implantable device 10 may be located in and/or received in the distal holding section 108. In the method 200, the emitted electrical signals may be directed 204 through one or more electrical ports 147 in the distal holding section 108 to exterior of the distal holding section 108. The directing of the electrical signals may inhibit the electrical signals from traveling between the second electrode 22 and the first electrode 20 within the distal holding section 108. The directed electrical signals pass through blood and/or tissue exterior of the distal holding section 108 and may re-enter through the distal opening 144 of the distal holding section 108 to be received 206 at the first electrode 20 (e.g., a second portion) of the implantable device 10. In some cases, the first electrode 20 of the implantable device 10 may be located distal of the second electrode 22.

In some cases, the electrical ports 147 through which the electrical signals are directed may be at a location proximal of the second electrode 22 of the implantable device 10. In one example of directing 204 the electrical signals, the electrical barrier 50 may be utilized to inhibit signals from traveling within the distal holding section 108 between the second electrode 22 and the first electrode 20. Illustratively, in method 200, the barrier 50 may be located at any location along the implantable device between the second electrode 22 and the first electrode 20.

Directing the electrical signals (e.g., current) from the implantable device 10 to travel from the second electrode 22 to the first electrode 20 exterior the distal holding section 108, may result in increasing the voltage of the electrical signal by increasing the dipole length of the electrical signal when the implantable device 10 is acting as a receiver. Further, when the implantable device 10 is acting as a transceiver, directing the electrical signals to travel between electrodes 22, 20 exterior of the distal holding section 108 may reduce and/or eliminate loss of current around the implantable device 10 due to overcrowding within the distal holding section 108.

The materials that can be used for the various components of the delivery devices, such as delivery device 100 (and/or other delivery structures disclosed herein) and the various members disclosed herein may include those commonly associated with medical devices. For simplicity purposes, the following discussion makes reference the delivery device 100 and components of thereof. However, this is not intended to limit the devices and methods described herein, as the discussion may be applied to other similar delivery systems and/or components of delivery systems or devices disclosed herein.

The delivery device 100 and/or other components of delivery system may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the delivery device 100 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method of directing electrical signals from a leadless pacing device received in a distal holding structure attached to a distal end of a delivery catheter, the method comprising:
    emitting electrical signals from a first electrode of the leadless pacing device received in the distal holding structure of the delivery catheter;
    directing the emitted electrical signals exterior of the distal holding structure through electrical ports in the distal holding structure at a location proximal of the first electrode of the leadless pacing device;
    receiving the emitted electrical signals directed exterior of the distal holding structure at a second electrode of the leadless pacing device within the distal holding structure, wherein the second electrode of the leadless pacing device is located distal of the first electrode of the leadless pacing device; and
    preventing the emitted electrical signals from traveling from the first electrode to the second electrode within the distal holding structure by providing an electrical barrier positioned within the distal holding structure such that the first electrode is located proximal of the electrical barrier and the second electrode is located distal of the electrical barrier.

2. The method of claim 1, wherein the first electrode is positioned on a proximal end of the leadless pacing device and the second electrode is positioned on a distal end of the leadless pacing device.

3. The method of claim 1, wherein the electrical barrier at least partially fills a radial space between an exterior surface of the leadless pacing device and an inner surface of the distal holding structure.

4. The method of claim 3, wherein the electrical barrier extends circumferentially around the exterior surface of the leadless pacing device.

5. The method of claim 4, wherein the electrical barrier fills an entirety of the radial space between the exterior surface of the leadless pacing device and the inner surface of the distal holding structure.

6. The method of claim 3, wherein the electrical barrier extends radially from the exterior surface of the leadless pacing device.

7. The method of claim 3, wherein the electrical barrier extends radially from an interior surface of the distal holding structure.

8. The method of claim 1, wherein the electrical barrier includes a nonconductive gel configured to prevent electrical signals from passing from a proximal side of the electrical barrier to a distal side of the electrical barrier.

9. The method of claim 1, further comprising providing fluid to a cavity within the distal holding structure, wherein the electrical barrier is configured to allow the fluid to pass from a proximal side to a distal side of the electrical barrier, but prevent electrical current from passing from the proximal side to the distal side of the electrical barrier when the fluid is not crossing the electrical barrier.

10. The method of claim 9, wherein the electrical barrier includes a first portion having a first tension or stiffness and a second portion having a second tension or stiffness different than the first tension or stiffness.

11. The method of claim 10, wherein the first tension or stiffness is less than the second tension or stiffness and the first portion flexes or deflects to allow the fluid to pass through the electrical barrier in response to a pressure greater than a threshold pressure to the first portion, thereby allowing fluid to pass through the first portion.

12. A method of directing electrical signals from a leadless pacing device received in a distal holding structure attached to a distal end of a delivery catheter, the method comprising:
    emitting electrical signals from a first electrode of the leadless pacing device received in the distal holding structure of the delivery catheter;
    directing the emitted electrical signals exterior of the distal holding structure at a first end of the distal holding structure;
    receiving the emitted electrical signals at a second electrode of the leadless pacing device inside a second end of the distal holding structure; and
    preventing the emitted electrical signals from traveling from the first electrode to the second electrode within the distal holding structure by providing an electrical barrier positioned within the distal holding structure such that electrical barrier is located only axially between the first electrode and the second electrode.

13. The method of claim 12, wherein the first end of the distal holding structure is a proximal end, wherein directing the emitted electrical signals exterior of the distal holding structure includes directing the emitted electrical signals through electrical ports in the distal holding structure at a location proximal of the first electrode of the leadless pacing device.

14. The method of claim 12, wherein the electrical barrier at least partially fills a radial space between an exterior surface of the leadless pacing device and an inner surface of the distal holding structure.

15. The method of claim 12, wherein the electrical barrier includes a nonconductive gel configured to prevent electrical signals from passing from a proximal side of the electrical barrier to a distal side of the electrical barrier.

16. The method of claim 12, further comprising providing fluid to a cavity within the distal holding structure, wherein the electrical barrier is configured to allow the fluid to pass from a proximal side to a distal side of the electrical barrier, but prevent electrical current from passing from the proximal side to the distal side of the electrical barrier when the fluid is not crossing the electrical barrier.

17. A method of directing electrical signals from a leadless pacing device received in a distal holding structure attached to a distal end of a delivery catheter, the method comprising:
    emitting electrical signals from a first electrode on a proximal region of the leadless pacing device received in the distal holding structure of the delivery catheter;
    directing the emitted electrical signals proximally through electrical ports in a proximal end of the distal holding structure and exterior of the distal holding structure;

allowing the emitted electrical signals to travel outside the distal holding structure from the proximal end to a distal end of the distal holding structure;

receiving the emitted electrical signals at a second electrode of the leadless pacing device inside the distal end of the distal holding structure; and preventing the emitted electrical signals from traveling from the first electrode to the second electrode within the distal holding structure by providing an electrical barrier positioned within the distal holding structure such that the first electrode is located proximal of the electrical barrier and the second electrode is located distal of the electrical barrier.

\* \* \* \* \*